United States Patent [19]

Kaitz et al.

[11] Patent Number: 4,860,736
[45] Date of Patent: Aug. 29, 1989

[54] FINGERNAIL SOLUTION APPLICATOR PAD AND NUTRIENT SOLUTION KIT

[75] Inventors: Richard A. Kaitz, Golden Valley; Miriam J. Kaitz, Minneapolis, both of Minn.

[73] Assignee: Miriam Collins - Palm Beach Laboratories Co., Minneapolis, Minn.

[21] Appl. No.: 157,297

[22] Filed: Feb. 17, 1988

[51] Int. Cl.4 ............................................. A61F 13/00
[52] U.S. Cl. .................................... 128/155; 128/156; 132/73; 132/75; 604/289; 604/290; 604/304; 604/305; 604/307; 604/308
[58] Field of Search ............... 604/289, 290, 304, 305, 604/307, 308; 132/73, 79 A; 128/155; 206/441

[56] References Cited

U.S. PATENT DOCUMENTS 2,431,203 11/1947 Sebastian .
2,563,689 8/1951 Muhlhauser .
2,703,083 3/1955 Gross .................................. 128/156
2,807,262 9/1957 Lew .
3,212,495 10/1965 Osbourn .
3,464,408 9/1969 Hamlin .
3,580,254 5/1971 Stuart ............................... 206/441 X
4,053,053 10/1977 Tumangday ......................... 206/441

Primary Examiner—Richard J. Apley
Assistant Examiner—N. Paul
Attorney, Agent, or Firm—Merchant, Gould, Smith, Edell, Welter & Schmidt

[57] ABSTRACT

An applicator which is designed to fit over a fingernail or toenail to apply a liquid solution to the nail region is provided. The applicator is mounted on a removable backing which has a hole therein to permit application of a liquid nail and cuticle nutrient to the applicator prior to removing it and affixing it on a finger or toe.

The applicator is generally in the shape of a triangle with a base, two sloping sides, and an apex opposite the base. The applicator inner side is adhesively coated and contains an absorbent pad section which is designed to receive the liquid nutrient solution and to apply that solution to the nail and cuticle of the finger or toe on which the applicator is attached.

1 Claim, 1 Drawing Sheet

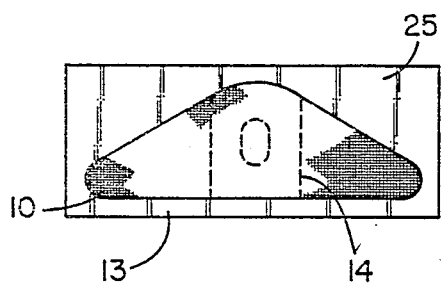
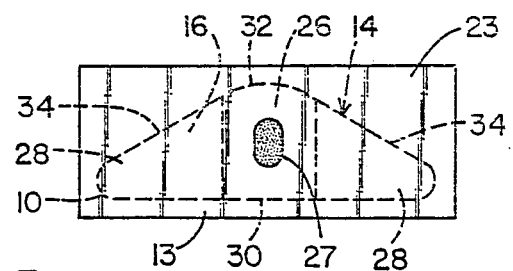
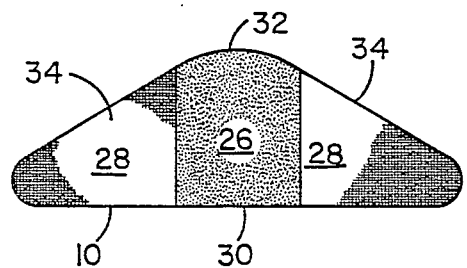
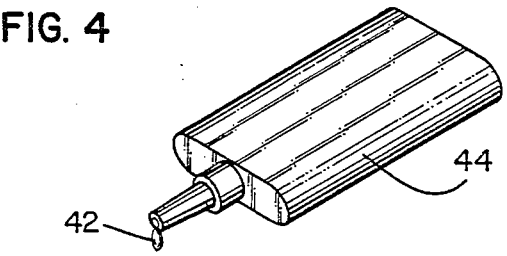
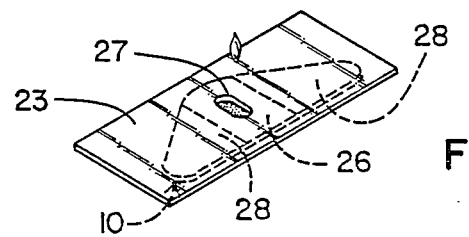
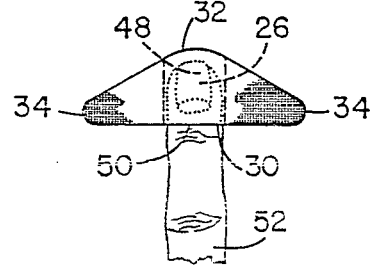
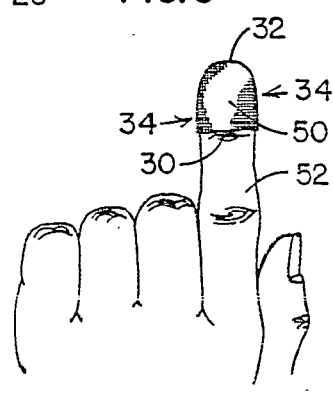

FINGERNAIL SOLUTION APPLICATOR PAD AND NUTRIENT SOLUTION KIT

BACKGROUND OF THE INVENTION

The present invention relates to a nail nutrient applicator kit which is characterized by the ability to apply liquid nail nutrient to a pad and adhesive tape applicator prior to affixing the triangular applicator onto a fingernail or toenail area. The applicator is removably attached to a mounting sheet which has a hole therein to permit application of a liquid nail and cuticle nutrient solution onto the underlying applicator. The mounting sheet is ten removed and the applicator is placed on the finger or toe.

In general, it has been found that many persons suffer from thin, delicate nails and rough, splitting cuticles which are in need of treatment to strengthen and beautify the nails, as well as to soften and control skin texture in the cuticle area. A prolonged topical application of a liquid nail and cuticle nutrient would penetrate and nourish the nail root area and in turn produce a strong nail outgrowth. Simultaneously, such application would soften the nail cuticle in the area closely adjacent to the hard nail to eliminate the tearing and abrasion of that skin. A continuous application of such nutrient over a period of from two to ten hours is necessary to insure therapeutic treatment to the area. Due to the time period required for nutrient application and the normal activities of the fingers and the toes, a protective applicator is necessary which will insure sufficient liquid availability and prolonged exposure for penetration of the nutrient.

It is accordingly one object of the present invention to provide a protective applicator which conforms to the particular dimensions of the nail region of a finger or toe. Conventional, rectangular bandages do not adequately conform to these nail areas resulting in bandage slippage and entry of foreign material underneath the bandage. A further difficulty of such conventional bandage products is their tendency to crumple near the fingertip or toetip. Yet another problem with such conventional bandage shapes is the susceptibility of the bandage to be pulled away from the finger or toe when caught or brushed against another object. Further disadvantages of conventional bandage-type applicators involve reduction of dexterity of the fingers and toes, impairment of the sense of touch to the pads of the fingers and toes, and general unsightliness of the bandages.

Several means have previously been employed for applying protective coverings and bandages to tip and nail areas of fingers and toes. One method of bandaging is disclosed in U.S. Pat. No. 2,431,203 issued on Nov. 18, 1947, to R. H. Sebastian. The Sebastian bandage is designed to cover the entire tip of the finger and comprises basically a bandage with a pair of side adhesive panels which can be folded over and around a finger to hold the bandage in place. The Sebastian bandage is cross-shaped. The bandage also has holes in the adhesive covering to act as vents near the tip of the finger.

In U.S. Pat. No. 2,563,689 issued on Aug. 7, 1951, to F. Muhlhauser, a protective fingernail covering is disclosed. The Muhlhauser patent has an anchor-type shape and does not have any holes. Neither the Sebastian or the Mulhauser patents disclose any mechanism for applying a liquid to the bandage either before or after placement on the finger area.

U.S. Pat. No. 3,464,408 issued on Sept. 2, 1969, to R. G. Hamlin discloses a special form of triangular bandage designed for relieving ingrown toenails. The Hamlin bandage is quite different from the present invention. Although medication can be applied with the Hamlin bandage, it is applied to the tissue area underneath the nail rather than to the nail or cuticle regions as in the present invention. This Hamlin toenail bandage does not contain any holes through which any medicine or nutrients could be applied. Rather, the medicine is pre-applied to a small portion of the bandage designed for placement beneath the corners of the forward part of the toenail. Such a bandage is not designed to protect the area around the base, or cuticle, of the toenail or any top portion of the toenail itself. The Hamlin bandage, as disclosed, may also require further protective coverings and bandages around the entire toe to be securely fastened.

Other patents disclose bandages with holes in the bandage. In U.S. Pat. No. 2,807,262 issued on Sept. 24, 1957 to R. B. Lew, a plastic adhesive-type bandage is shown which has holes in the center portion of the adhesive material so that medication can be applied through the bandage to a wound. The Lew bandage is different from the present invention because there are no holes in the adhesive material in the latter. Furthermore, the Lew invention does not disclose a hole through a removable backing material to permit the bandage to be saturated before it is applied.

In U.S. Pat. No. 3,212,495 issued on Oct. 19, 1965, to R. A. Osbourn, et al., a bandage-like test patch is disclosed. The Osbourn test patch construction has an adhesive backing material, an absorbent material, and a cover sheet with an opening therein. The pad can be saturated with liquid material through the opening and the entire patch is then applied to the skin to see whether the liquid material will irritate the skin. The Osbourn test patches come with a removable cover strip which protects the patches prior to use. However, there are no openings through the cover strips which allow insertion of any liquid. Therefore, the cover strips must be completely removed before using the test patches.

In the Osbourn patent, the cover sheet with a hole in it remains in place during use. The purpose of that hole is to limit the size of exposure and possible allergic reaction of the patch wearer to the allergen contained within the test patch. In the present invention, the mounting sheet is removed and discarded prior to attachment of the applicator pad. Moreover, the purpose of the hole in the mounting sheet of the present invention is to allow sufficient liquid to be dispersed for saturation throughout all of the applicator pad rather than to restrict the wearer's exposure to merely the size of the hole. Therefore, once the mounting sheet is removed, the area of exposure of the present invention is actually much larger than the size of the hole through which the nutrients were placed onto the applicator.

SUMMARY OF THE INVENTION

This invention relates to an adhesive applicator system which has for an object an applicator designed to conformally adapt to the nail region of a finger or toe while applying a topical solution to that region. The applicator is removeably attached to a mounting sheet which has a hole therein to permit pouring of a liquid nail and cuticle nutrient solution onto the underlying applicator. The mounting sheet is removed prior to affixing the applicator onto the finger or toe.

In accordance with the present invention there is provided a nail solution applicator kit which is comprised of an applicator and a mounting sheet. The applicator has an outer and an inner side with the inner side having an absorbent section and an adhesive section. The mounting sheet contains a hole which allows for nail nutrient liquid to be placed onto the underlying applicator absorbent section prior to removal of the applicator from the mounting sheet. After placing the nutrient onto the applicator, the mounting sheet is removed, and the absorbent section is positioned over the nail region of a finger or toe. The adhesive section of the applicator then assures secure fastening of the applicator while the nutrient solution penetrates the region beneath the absorbent section.

The applicator is designed to provide continuous protection and application of the nutrient contained therein to the fingernail or toenail areas. The triangular design of this invention uniquely conforms the applicator pad to the area of interest on a finger or toe without the disadvantages of the prior art noted above. A further object of this invention is the manner in which the nutrient solution is applied to the applicator prior to removal of the backing material. The objective is to provide a nonmessy and efficient method of preparing this nutrient applicator for positioning on the finger or toe area.

Other objects of this invention will in part be obvious and in part hereinafter pointed out.

BRIEF DESCRIPTION OF THE DRAWINGS

While the specification concludes with claims particularly pointing out and distinctly claiming the subject matter as forming the present invention, it is believed that the invention will be better understood from the following description taken in connection with the accompanying drawings in which, FIG. 1 is a plan view of the applicator and attached mounting sheet with the outer side of the applicator facing upwardly.

FIG. 2 is a plan view of the applicator attached to and beneath the mounting sheet.

FIG. 3 is a plan view of the applicator with the inner side adhesive and absorbent surfaces facing upwardly.

FIG. 4 is a perspective view showing the manner of applying the nutrient to a preferred embodiment of the invention.

FIG. 5 is an environmental illustration of the applicator applied to the nail region of a finger prior to adhesive attachment.

FIG. 6 is an environmental illustration of the protective applicator adhesively attached to a finger; the attachment providing a conformal fit of the applicator to the nail region of the finger.

DETAILED DESCRIPTION WITH PREFERRED EMBODIMENTS

Referring to FIGS. 1-3, there is shown a preferred embodiment of a nail solution applicator system which is comprised of an applicator 10 and a mounting sheet 13. Applicator 10 is preferably constructed of a vinyl material with a non-adhesive outer side 14, and an adhesive inner side 16. The mounting sheet 13 has a top side 23 and a bottom side 25. The adhesive inner side 16 of applicator 10 provides for adhesively mounting applicator 10 on mounting sheet 13 so that, when removed, the adhesive inner side 16 may be reattached to a user's finger or toe. Bottom side 25 of mounting sheet 13 is coated with a wax-like substance so that applicator 10 can be easily removed therefrom. In a preferred embodiment, bottom side 25 of mounting sheet 13 is attached to adhesive inner side 16 of applicator 10.

Preferably, applicator 10 is generally in the shape of a triangle with an absorbent pad 26 attached to a central portion of applicator 10 inner side 16. Also, in a preferred embodiment, mounting sheet 13 includes an aperture or hole 27 located to provide open communication between mounting sheet top side 23 and absorbent pad 26. Absorbent pad 26 is intermediately disposed between two adhesive end sections 28 of applicator 10. The generally triangular shape of applicator 10 includes a base 30 which, in a preferred applicator, may be elongated. An apex 32 is located opposite base 30. Apex 32 is formed by the intersection of sloping sides 34 which extend from base 30.

In FIG. 2, applicator 10 is positioned with its outer side 14 facing down and with mounting sheet 13 attached to the upwardly facing, but underlying, applicator inner side 16. On applicator inner side 16, absorbent pad 26 is intermediately positioned between two adhesive end sections 28 and extends from base 30 to apex 32. A hole 27 is placed in mounting sheet 13 through which a nutrient is applied directly to the applicator absorbent pad 26.

FIG. 3 shows the absorbent pad 26, preferably made of a cotton-like or gauze-like absorbent material, which is designed to receive and absorb a nutrient solution. Base 30 of absorbent pad 26 is designed to be in contact with the cuticle area of a fingernail or toenail, with apex portion 32 of absorbent pad 26 positioned at the forward most part of the same fingernail or toenail. The two adhesive end sections 28 of inner side 16 of applicator 10 are designed to securely fasten the applicator to a finger or toe.

As illustrated in FIG. 4, the nail solution applicator system is designed to receive a nutrient solution 42 through hole 27 in mounting sheet 13. Preferably, the nutrient solution 42 is applied to applicator 10 when applicator outer side 14 is facing down, with mounting sheet top side 23 facing upwardly but in adhesive attachment to applicator 10. The location of mounting sheet hole 27 is above and in line with the center of absorbent pad 26. This location provides optimal placement of the nutrient solution onto applicator 10. The shape of hole 27 is generally approximately the shape of absorbent pad 26 and, therefore, the shape encourages application of the nutrient solution in a manner which equally distributes the nutrient solution throughout absorbent pad 26. Accordingly, when applicator 10 is placed on a finger or toe the entire nail and cuticle area of the finger or toe which is beneath absorbent pad 26 will receive a proper amount of nutrient solution for absorption. The size and shape of hole 27 in relation to absorbent pad 26 further prevents spillage onto adhesive end sections 28 of the applicator so as to promote longer adhesion.

The liquid nutrient solution 42 used with the present invention is preferably dispensed from a dropper type container or tube 44 designed for 3-4 drops per absorbent section. Further, nutrient solution 42 is preferably a liquid which is generally comprised of nutrients including elastin, lecithin, and other vitamins and proteins. The optimal duration for applying nutrient solution 42 to a nail and cuticle varies from approximately 3-10 hours. Although applicator 10 is not easily removed by normal activity of the fingers or toes, it is quickly removed after treatment is complete.

FIG. 5 shows a preferred orientation of applicator 10 on a fingernail region 48. Base 30 of applicator 10 is positioned generally in contact with the cuticle area 50 of finger 52. Absorbent pad 26 provides a protective covering as well as a liquid nutrient applicator to the entire fingernail region 48. Applicator 10 depicted in FIG. 5 includes sloping sides 34 which are shown prior to adhesive attachment to the finger 52.

FIG. 6 shows a preferred method of attaching applicator 10 to a fingernail region. Base 30 of absorbent pad 26 is positioned in contact with cuticle area 50 of finger 52. Apex portion 32 of absorbent pad 26 is positioned in contact with the forwardmost portion of the fingernail. The sloped sides 34 of applicator 10 extend around the sides and bottom of the finger 52. The sloped design of the sides 34 provides a more conformal fit of the applicator to the finger, and thereby prevents the entry of foreign material beneath the absorbent pad section of the applicator. This conformal fit also minimizes the risk of catching, and self-removing, the forward part of applicator 10 on an object when the fingers and toes are moved during normal activity. Such a tendency to catch on other objects is a common problem of conventional bandage-like applicators, and is therefore a problem in the art which has been solved by this design. The conformally sloped sides 34, when attached to a finger or toe, also minimize the tendency noted in other types of applicators to self-attach and crumple near the forward part of the finger or toe. The self-attachment problem creates undesired pockets of dirt and other matter which may collect near the nail and cuticle, thereby degrading the protection which the bandage or applicator is supposed to be providing.

The proper fit and positioning of any applicator to a finger or toe is critical to the comfort and protection provided by that applicator. This invention provides for a system of applying a nutrient solution to an applicator in a manner which allows equal distribution of the nutrient solution on the nail and cuticle region of a finger or toe. Moreover, the invention insures a conformal fit of the applicator to the finger or toe so that greater protection and longer wear is achieved by this applicator.

The invention accordingly consists in the features of construction, combinations of elements, and arrangement of parts which will be exemplified in the construction described above and of which the scope of the invention will be indicated in the following claims.

What is claimed is:

1. A nail solution applicator kit, comprising:
   an applicator comprising a backing member having an outer side and an inner side, said inner side having an adhesive coating, said adhesive coating providing for removably attaching said backing member to a finger or toe, and said inner side further having an absorbent pad centered and permanently affixed thereon;
   a container of liquid nutrient solution, said solution for application to said absorbent pad;
   a mounting sheet having a top and a bottom side, said bottom side having a wax-like, nonabsorbent, coating for permitting said backing member and absorbent pad to be adhesively and removeably affixed thereon, said mounting sheet also having a hole therein, said hole being disposed in line with said absorbent pad for application of said liquid nutrient solution through said hole to said absorbent pad, said backing member and absorbent pad being removable from said mounting sheet for adhesive attachment to a finger or toe, with said absorbent pad being oriented across the cuticle and nail area of the finger or toe; and
   said applicator being generally in the shape of a triangle with an elongated base and two sides sloping to an apex opposite said base, said applicator thereby being constructed and arranged to be adhesively secured to a finger or toe with said pad disposed over the nail, with said base being oriented across the back end or cuticle area of the nail and with said apex being at the forward end of the finger or toe, said generally triangular shape providing improved conformal attachment of said applicator to said finger or toe.

* * * * *